United States Patent

Turbanti et al.

[11] Patent Number: 5,095,137
[45] Date of Patent: Mar. 10, 1992

[54] AMIDES OF CYCLOMETHYLEN-1,2-BICARBOXYLIC ACIDS HAVING THERAPEUTICAL ACTIVITY

[75] Inventors: Luigi Turbanti; Guido Cerbai, both of Pisa; Marco Criscuoli, Scandicci, all of Italy

[73] Assignee: Laboratori Guidotti Spa, Pisa, Italy

[21] Appl. No.: 595,639

[22] Filed: Oct. 9, 1990

Related U.S. Application Data

[63] Continuation of Ser. No. 336,407, Apr. 11, 1989, abandoned.

Foreign Application Priority Data

Apr. 2, 1988 [IT]  Italy .................. 20172 A/88

[51] Int. Cl.$^5$ ......................... C07C 205/00
[52] U.S. Cl. ..................... 560/125; 560/39; 560/41; 560/105; 560/106; 560/118; 560/123; 560/251; 560/312; 562/448; 562/450; 562/500; 562/504; 562/507; 562/505
[58] Field of Search ............ 562/500, 448, 504, 505, 562/450, 507; 560/1, 105, 106, 122, 123, 125, 251, 312, 39, 41, 168

*Primary Examiner*—Michael L. Shippen
*Attorney, Agent, or Firm*—Armstrong, Nikaido Marmelstein, Kubovcik and Murray

[57] ABSTRACT

The amides of cyclomethylen-1,2-bicarboxylic acids having the formula:

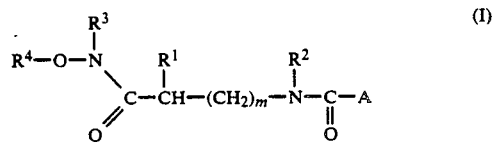

(I)

wherein
A represents

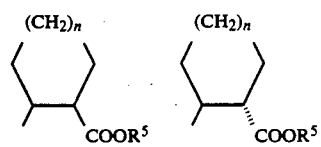

$R^1$ represents —H, —CH$_3$, —CH$_2$—CH$_3$, —CH(CH$_3$)$_2$,

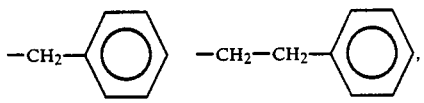

$R^2$ represents —H, CH$_3$, —CH$_2$—CH$_3$, —CH(CH$_3$)$_2$, —CH$_2$—CH$_2$—CH$_3$, —CH$_2$—CH(CH$_3$)$_2$—CH$_2$—CH$_2$—CH$_2$—CH$_3$, —CH$_2$—C$_6$H$_5$, —C$_6$—H$_5$;
$R^3$ represents —H, —CH$_3$, —C$_2$H$_5$,

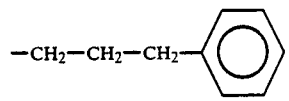

$R^5$ represents —H, —CH$_3$, —C$_2$H$_5$, —CH$_2$C$_6$H$_5$,

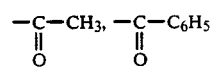

Y = —H, —CH$_3$, —CH(CH$_3$)$_2$
Z = —H, —CH$_3$, —C(CH$_3$)$_3$, —CH(C$_2$H$_5$)$_2$,

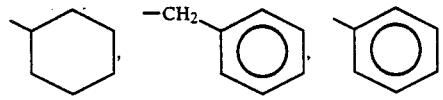

$R^4 = R^5$,

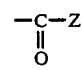

m is 0 or 1 and n is an integer varying between 0 and 3, are endowed with ACE-inhibiting activity and are thus therapeutically useful as anti-hypertension agents.

For their preparation cyclomethylene-1,2-bicarboxylic acid or a derivative thereof is condensed either with an amino derivative containing a protected hydroxamic group, or with an aminoester, and then in the former case the protecting group is removed, or in the latter case is reacted with either hydroxylamine or N-alkylhydroxylamine.

50 Claims, No Drawings

AMIDES OF CYCLOMETHYLEN-1,2-BICARBOXYLIC ACIDS HAVING THERAPEUTICAL ACTIVITY

This application is a continuation of application Ser. No. 336,407 filed Apr. 11, 1989, now abandoned.

The present invention relates to a series of novel amides of cyclomethylen-1,2-bicarboxylic acids with amino-hydroxamic acid having anti-hypertension activity, to the processes for their preparation and to the pharmaceutical compositions containing them.

The compounds of the present invention are represented by the following general formula:

$$R^4-O-N(R^3)-C(=O)-CH(R^1)-(CH_2)_m-N(R^2)-C(=O)-A \quad (I)$$

wherein
A represents

[cyclohexyl with COOR$^5$ substituent, (CH$_2$)$_n$] , [cyclohexyl with COOR$^5$ substituent (stereo), (CH$_2$)$_n$]

$R^1$ represents —H, —CH$_3$, —CH$_2$—CH$_3$, —CH(CH$_3$)$_2$,

—CH$_2$—C$_6$H$_5$, —CH$_2$—CH$_2$—C$_6$H$_5$,

—CH$_2$—CH$_2$—CH$_2$—C$_6$H$_5$ $R^2$ represents —H, CH$_3$, —CH$_2$—CH$_3$, —CH(CH$_3$)$_2$, —CH$_2$—CH$_2$—CH$_3$, —CH$_2$,—CH(CH$_3$)$_2$ —CH$_2$—CH$_2$—CH$_2$—CH$_3$, —CH$_2$—C$_6$H$_5$, —C$_6$—H$_5$;
$R^3$ represents —H, —CH$_3$, —C$_2$H$_5$, $$-\underset{\underset{O}{\|}}{C}-CH_3, \quad -\underset{\underset{O}{\|}}{C}-C_6H_5$$

$R^5$ represents —H, —CH$_3$, —C$_2$H$_5$, —CH$_2$—C$_6$H$_5$, $$-\underset{Y}{\overset{|}{HC}}-O-\underset{\underset{O}{\|}}{C}-Z$$

Y=—H, —CH$_3$, —CH(CH$_3$)$_2$
Z=—H, —CH$_3$, —C(CH$_3$)$_3$, —CH(C$_2$H$_5$)$_2$,

[cyclohexyl-CH$_2$—], [benzyl —CH$_2$—], [phenyl]

$R^4=R^5$, $$-\underset{\underset{O}{\|}}{C}-Z$$

m is 0 or 1 and n is an integer varying between 0 and 3,

More specifically the compounds of the present invention consist of a series of amides of cyclomethylen-1,2-bicarboxylic acids having cis or trans configuration, bonded to the primary or secondary amino group of an aminohydroxyamic acid.

The compounds of the invention are endowed, on the basis of the results of the in vitro tests, with an inhibiting action against ACE (the enzyme by which angiotensin I is converted into the powerful endogenous pressure agonist angiotensin II) and with an anti-hypertension activity, to be considered as related to the former one, which is revealed for some compounds in the spontaneously hypertensive rat and particularly in the animal, either awake or anasthetized affected by hypertension induced from angiotension I.

For the treatment for the several forms of artherial hypertension ACE-inhibiting drugs are known and widely used, which are also employed for the treatment of the congestive cardiac decompesation.

The first and main ACE-inhibiting drug has been and is the 1-(3-mercapto-2-methyl-propionyl)-1-pyrrolidin 2-carboxylic acid, also known with the non chemical name (DCI) of captopril and having the formula:

$$HS-CH_2-CH(CH_3)-C(=O)-N\text{-pyrrolidine-COOH} \quad (II)$$

Presently, besides captopril, other ACE-inhibiting agents used in pharmaceutical field on worldwide scale are enalapril and lysinopril. It is believed that the therapeutical action of these compounds takes mainly place through the inhibition of the conversion enzyme of angiotensin I, both plasmatic and of determined tissue systems, with the attendant reduction of the levels of the powerful endogenous pressure antagonist angiotensin II.

On the other side, owing to the fact that the ACE-inhibition causes also the metabolism of bradykinin to be reduced, the increase of the levels of this vasodilating and diuretic agent might partially explain the anti-hypertension action of the subject drugs.

In the cases of hypertension combined with low levels of angiotensin II, the effect of the ACE inhibitors might be attributed to an indirect action owing to the interference with the neurogenic vasalconstriction (by which the nervious-sympatic transmission is made easier).

The compounds of the present invention are distinguished with respect to the above compounds and with respect to the other ACE-inhibitors disclosed in the literature since their carboxylic end portion (probably capable of interacting with determined active centers of the ACE enzymes) consists of an amide of a cyclomethylen-1,2-bicarboxylic acid (formula IIIa) whereas in all the known ACE-inhibitors this portion consists of an amide of cyclic or linear aminoacids (formulae IIIb and c).

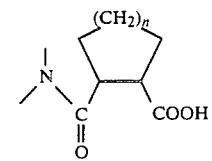
IIIa

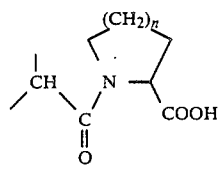
IIIb

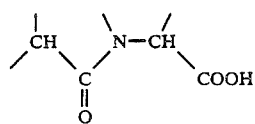
IIIc

Owing to this chemical feature which is common to all the compounds of the invention, these compounds, besides the novelty, possess with a self-evident structural originality feature with respect to the known compounds, by which these compounds are endowed with original characteristics also as regards the pharmacotherapeutical properties.

From the pharmacological point of view the compounds of the invention are endowed, as already mentioned, with an ACE-inhibiting action which has been evaluated in the in vitro tests, which, in the test of functional activity, gives place to a readily appearing and long lasting anti-hypertension effect.

Another object of the present invention are the processes for the preparation of the compounds of formula (I).

According to the first process cyclomethylen-1,2-bicarboxylic acid, particularly its acidic portion, is condensed with an amino derivative having an alkyl or benzyl substituted hydroxamic group.

The condensation product, in turn, if the substituting group is benzyl, undergoes a catalytic hydrogenation for the removal of the benzyl group and thus obtain a compound of formula (I) wherein $R^3$ and $R^4$ are hydrogen. Within this process the condensation step can be carried out in two ways, namely:

Method a) through the reaction of said amino derivative with the anhydride of the cyclomethylen-1,2-bicarboxylic acid, Method b) through the reaction of said amino derivative with the bicarboxylic acid in the presence of a condensating agent. The latter is of known type and preferably is either ethyl-N'-/3-dimethyl-aminopropyl/carbodiimide (WSC) or dicyclohexylcarbodiimide (DCC).

According to a second process the condensation is carried out starting from amino esters as in the first process, whereby the corresponding amido derivatives are prepared and then converted into the corresponding hydroxamic derivative by reaction with hydroxylamine or N-alkylhydroxylamine, wherein alkyl means methyl and ethyl.

In this case too, both methods, (a) and (b), of condensation, as above mentioned, are foreseen.

Lastly, according to a third process useful for the preparation of the compounds of the invention of formula (I), wherein m=1, the anhydride of the bicarboxylic acid or the cyclomethylen-1,2-bicarboxylic acid itself are directly condensed with the amino-hydroxamic acid.

According to a fourth process, an alkyl monoester of a cyclomethylenl,-2-bicarboxylic acid is condensed with an amino derivative having an hydroxamic group protected with a benzyl group.

The resulting amidoester is alternatively:

c) catalically hydrogenated to remove the benzyl group, leading to the compounds of formula (I) wherein $R^5$=methyl, ethyl;

d) subjected to alkaline hydrolysis and subsequent catalytic hydrogenation to obtain the compounds of formula (I) wherein $R^3=R^4=R^5=H$.

The amidohydroxamic acids obtained according to the processes as above shortly defined in turn may be used as the starting compounds for the preparation of further derivatives encompassed by the general formula (I), through the reaction with an anhydride of formula:

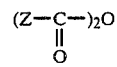

wherein Z has the already stated meaning, leading to the compounds of formula (I) wherein $R^3$ and/or $R^4$ represent

If, on the contrary, the amido intermediate obtained before the removal of the protecting benzyl group is reacted with an acyloxy-methyl halide, an intermediate is obtained which, upon being catalytically hydrogenated for the removal of the benzyl group, leads to a derivative of formula (I) wherein

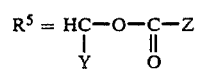

in which Y and Z have the above indicated meanings.

Lastly, if a compound of formula (I) wherein $R^5=CH_3$, $C_2H_5$, $C_6H_5-CH_2$, is reacted with an acyloxy-methyl halide and from the resulting intermediate compound the protecting group at the starting esterified carboxylic function is removed, there are obtained the compounds of formula (I) wherein

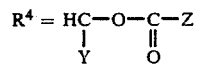

The following schemes illustrate synthetically the above defined processes.

SCHEME 1
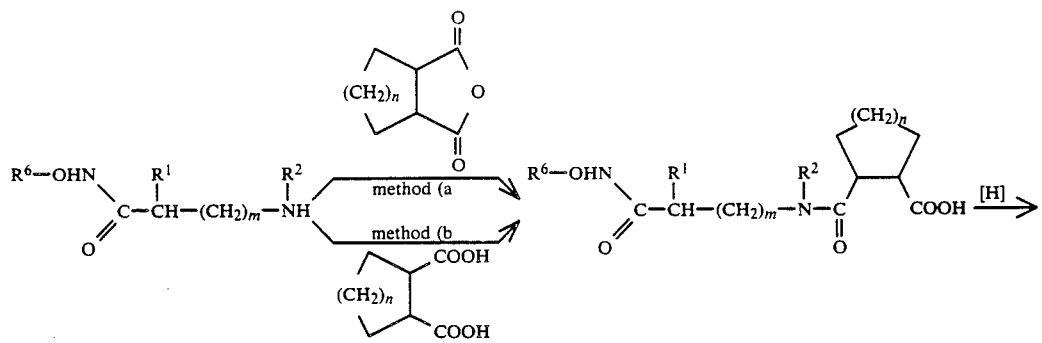
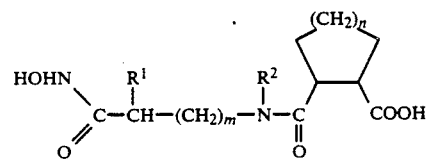
SCHEME 2
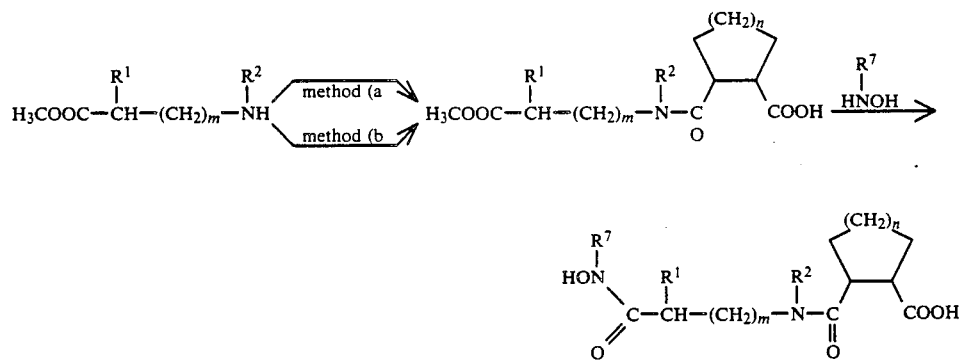
SCHEME 3
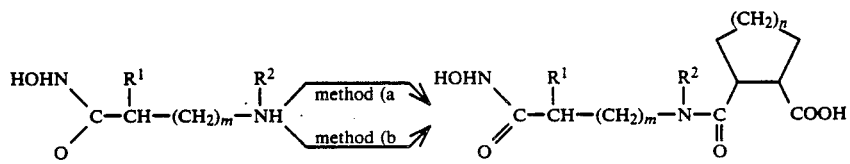
SCHEME 4
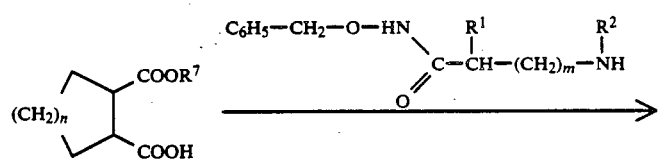

-continued
SCHEME 4
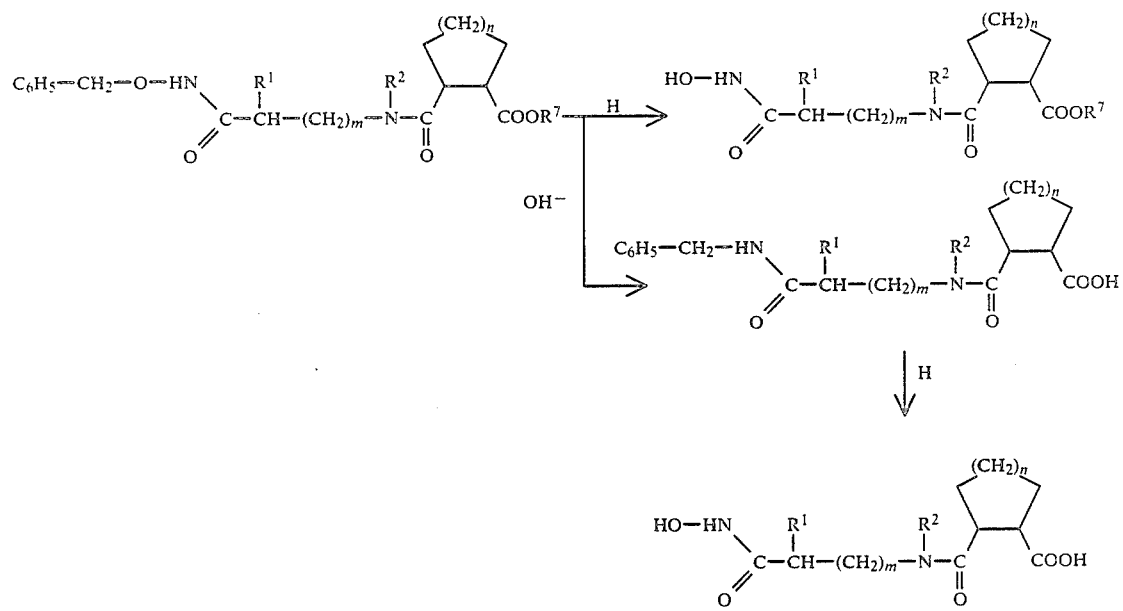
SCHEME 5
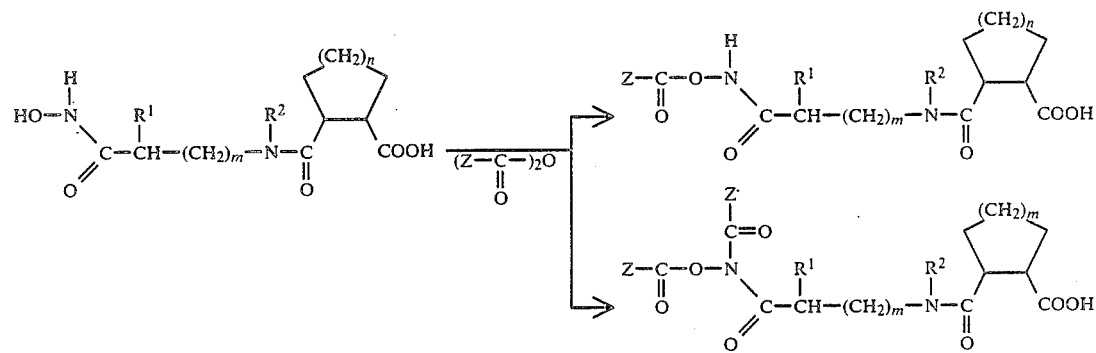
SCHEME 6
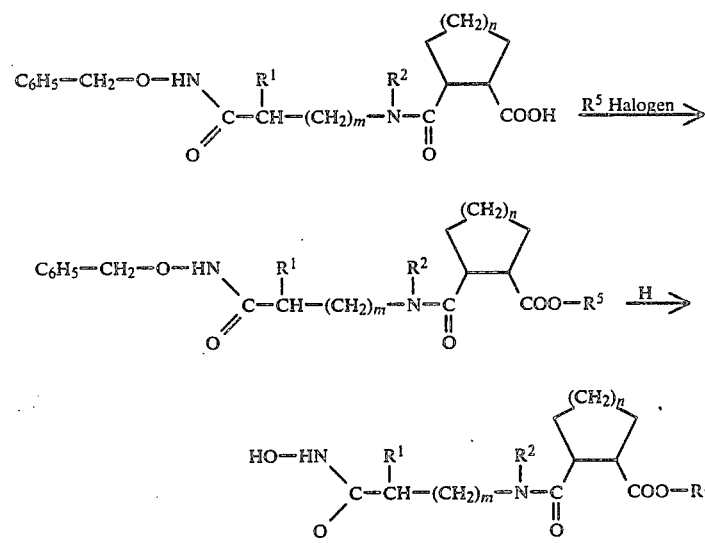

SCHEME 7

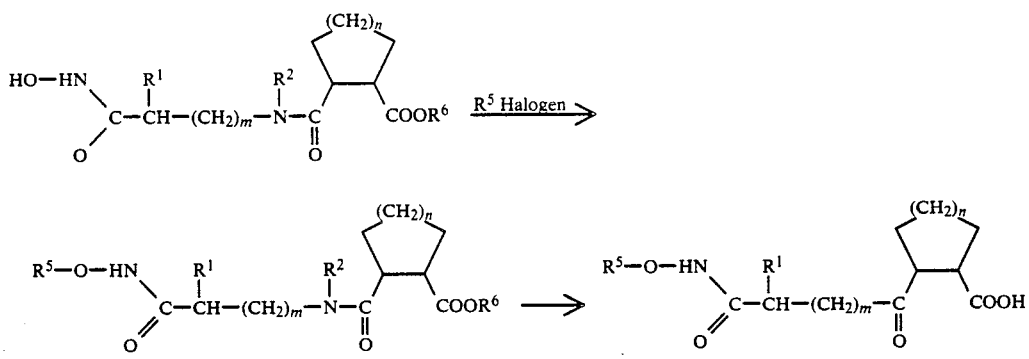

In the carrying out of the first process, the condensation step can be carried out in a solvent selected among water, aliphatic alcohols, such as for example methanol, ethanol, butanols, and chlorinated aliphatic solvents, such as methylene chloride, chloroform, dichloroethanes and at a temperature of between −5° C. and 60° C., care being taken of operating at low temperature (between −5° C. and the room temperature) when the reaction solvent is water or an aqueous mixture.

In turn the step of catalytic hydrogenation is carried out in aliphatic alcohols, such as methanol or ethanol, with hydrogen at room pressure and temperature in the presence of a standard catalyist such as Pd onto carbon.

In the carrying out of the second process, the condensation is carried out under with the same aforementioned conditions, whereas the next reaction with hydroxylamine contemplates the use of alcohols as water and the solvent and takes place at room temperature.

For the third process the condensation is carried out in aqueous alkaline environment at a temperature not higher than 40° C. and normally at room value.

Considering now the scheme 4, the first step takes place under the same conditions already indicated for the first process (scheme I), method (b).

The catalytic hydrogenation is likewise carried out, whereas for the alternative involving an alkalyne hydrolysis, the conditions thereof must be mild (namely room temperature, two hour time, water as the solvent). The schemes 5, 6 and 7, relate to the preparation of derivatives of formula (I) starting from end or intermediate compounds of the processes of the schemes 1 to 4, account being taken of the indicated meanings of the substitution groups.

More particularly in the scheme 5 there are prepared derivatives of formula (I)-O-acylated at the hydroxamic group; in this case the reaction with the anhydride is carried out at low temperature (lower than 20° C.) at least in the initial part, in the presence of catalytic amounts of 4-N,N'-dimethylamino pyridine.

In the schemes 6 and 7 the reaction with the acyloxymethyl halide is carried out at low temperature (lower than 20° C.) at least in the initial part, in anhydrous environment and under nitrogen.

The following examples illustrate the preparation of a few compounds according to the invention; it is meant that these examples have no limiting purpose.

Melting points were taken on a Kofler melting point apparatus and are uncorrected.

All compounds had I.R. and $^1$HNMR spectra consistent with their assigned structures and had elemental analyses within +0.4% of the calculated values except where noted.

Some solvents and reagents were indicated with commonly used abbreviations: THF=tetrahydrofuran, DCC=dicyclohexylcarbodiimide, ACOEt=ethylacetate, WSC=ethyl-N'-/3-dimethylaminopropyl/carbodiimide.

EXAMPLE 1

Cis-2-[[N-[2-(hydroxyamino)-2-oxoethyl]amino]carbonyl-cyclohexanecarboxylic acid To a solution of 1.2 g (4.07 mmoles) of O-benzyl-aminoacetohydroxamic acid trifluoroacetate in 30 ml of H$_2$O 1.0 ml of 4N NaOH are added, causing the precipitation of a crystalline product.

This suspension is added under stirring at room temperature with 0.628 g (4.07 mmoles) of 1,2-cyclohexanbicarboxylic anhydride and with 1.02 ml of 4N NaOH, portionwise, over a time of 1 hour so that the reaction mixture is maintained at pH 1.0 throughout all the addition time. The reaction mixture having opalescent aspect is maintained under stirring at room temperature for 2 hours and then, after filtration, the clear solution is made acidic at pH 1 with 10% HCl under cooling with ice, thus giving place to the percipitation of the O-benzylic amido derivative in form of ivory crystals, 0.9 g, yield 6%, m.p. 141°–143° C.

0.7 g (2.09 mmoles) of this O-benzylic intermediate, dissolved in 45 ml of ethanol are hydrogenated at room pressure and temperature in the presence of 10% Pd onto carbon. The calculated amount of hydrogen, 51 ml, is absorbed in about 4 hours. The ethanol solution, after filtration of the catalyst, is evaporated to dryness and the residue consisting of hygroscopic crystals is purified by crystallization from acetone leading to the expected amido derivative, 0.27 g yield 53%, m.p. 133°–135° C. (with decomposition).

EXAMPLE 2

Trans-2[[N-[2-(hydroxyamino)-2-oxoethyl]-N-ethylamino]carbonyl]- -cyclohexanecarboxylic acid A solution of 6 g (45.7 mmoles) of ethyl ethyl-aminoacetate in 130 ml of methylene chloride is added under stirring at 5° C. with 7.05 g (45.7 mmoles) of trans-1,2-cyclohexanbicarboxylic anhydride and the resulting solution is maintained at room temperature for 20 hours.

After a number of washings with 40 ml of 5% HCl and with two portions of 40 ml of saturated aqueous solution of sodium chloride, the reaction solution is dehydrated on anhydrous sodium sulphate and evaporated to dryness under vacuum to get 13 g (yield: 99%) of a chromatographically pure, white solid residue, consisting of the trans-2[[N-[2-(hydroxyamino)2-oxoethyl]-N-ethylamino]carbonyl]-cyclohexanecarboxylic acid. methyl-N-ethyl-carbamoyl-1-cyclohexancarboxylic acid.

The solution of 6 g (21.03 mmoles) of this acid in 30 ml of methanol is added under stirring at 5° C. with 2.77 g (69.4 mmoles) of NaOH in 30 ml of methanol, and, then, with 1.6 g (23.1 mmoles) of hydroxylamine hydrochloride.

The resulting suspension is reacted under vigorous stirring at 15° C. for 4 hours, then the reaction mixture is evaporated to dryness, under vacuum at room temperature to obtain 9.8 g of resinous, colorless residue. This residue is dissolved through stirring in 10 ml of water and the clear solution is made acidic up to pH 2 with 6N HCl, salted up to saturation with sodium chloride and lastly extracted with portions of 20 and 10 ml of ethyl acetate.

The combined organic extracts are dehydrated on MgSO4, and evaporated to dryness under vacuum to obtain 5.59 g of colorless crystalline residue. This product is taken with 50 ml of chloroform, and the resulting suspension is filtered under vacuum and the residue is treated with 90 ml of 1,2-dichloroethane to form a suspension which is maintained at rest at room temperature.

By filtration under vacuum 4.58 g are obtained (yield: 80%) of the expected product, as colorless crystals m.p. 137°–139° C. (Kofler).

EXAMPLE 3

Cis-2-[[N-[2-benzyl-3-(hydroxyamino)-3-oxopropyl]amino]carbonyl-cyclohexanecarboxylic acid A solution of 4 g (20.0 mmols) of 2-benzyl-3-aminopropionic-hydroxamic acid (prepared by reaction of the methylester of 2-benzyl-3-amino-propionic acid with hydroxylamine) in 70 ml of H2O and 6 ml of 4N NaOH, is added, under stirring and at the temperature of 20°–25° C., simultaneously, over 1 hour, with 3.1 g (20.0 mmoles) of 1,2-cyclohexanbicarboxylic anhydride and 4 ml of 4N NaOH maintaining the mixture at pH 11 for the whole addition time.

After 2 hours of stirring at 20°–25° C., the mixture is made acidic to pH 1 with 10% HCl and extracted with CHCl3. The CHCl3 is evaporated and the residue of ivory color is crystallized from acetate obtaining the expected compound in white crystalline form, 1.48 g, yield 26.6%, m.p. 171°–175° C.

EXAMPLE 4 cis-2[[N-[2-(hydroxyamino)-2-oxoethyl]-N-methylamino]carbonyl]-cyclohexanecarboxylic acid To a stirred solution of cis-cyclohexanedicarboxylic anhydride (1.60 g, 10.4 mmol) in dichloromethane (20 mL), under nitrogen, was added a solution of O-benzyl sarcosin hydroxamic acid trifluoroacetate (3.08 g, 10.0 mmol) and triethylamine (3.0 mL, 21.5 mmol) in dichloromethane (30 mL), and the mixture was washed with cold 5% HCL(10 cc×2), neutralized with 10% NaHCO3 and dried with MgSO4. The solvent was evaporated under reduced pressure and the residue was crystallized from aceton/ether to give the "O-benzylic amide" intermediate (3.40 g, 95%) as white crystals, m.p. 130° C. This compound (2.35 g, 6.75 mmol) was hydrogenated in methanol (30 mL) in presence of 10% Pd/C for 2 h. After evaporation of the solvents under reduced pressure at 5° C., the product was taken up in dichloromethane to give the title compound (1.25 g, 71%) as white crystals: m.p. 131°–133° C.

EXAMPLE 5

Cis-2-[[N-[2-oxoethyl]-N-phenylamino]carbonyl]-cyclohexanecarboxylic acid

A solution of 1.32 g (33 mmoles) of NaOH in 32 ml of methanol, is added under stirring at a temperature of 10° C., with 3.19 g (10 mmoles), of cis-2-[[N-[2-methoxy-2-oxoethyl]-N-phenylamino]carbonyl]-cyclohexanecarboxylic acid (prepared from the anhydride of the cis-1,2-cychlohexanbicarboxylic acid and methyl N-phenyl-aminoacetate according to a process like that disclosed in the example 2), and then with 0.764 g (11 mmoles) of hydroxylamine hydrochloride. The resulting suspension is maintained under stirring at 15° C. for 6 hours, then at rest for the night.

After evaporation up to dryness under vacuum, the residue is taken with 55 ml of water, the suspension is treated with "norite", filtered and lastly made acidic in cool situation with 105 HCl up to pH 3. The resinous precipitate is extracted with two portions of 60 ml of methylene chloride and the combined organic extracts are washed with water saturated with sodium chloride, dehydrated onto anhydrous sodium sulphate and evaporated under vacuum to give 2.7 g (yield 84%) of a colorless resinous solid residue. The latter is purified by dissolution in 27 ml of acetone, from which it precipitates again through extended resting at 0° C. leading to the expected compound as colorless crystals, m.p. 160°–161° C.

EXAMPLE 6

Trans-2[[N-[2-(hydroxyamino)-2-oxoethyl]-N-methylamino]carbonyl]cyclopentanecarboxylic acid.

1.16 g (7.34 mmoles) of trans-1.2-cyclopentanebicarboxylic acid are solubilized in a solution of H2O/t-butanol. The solution is added with 1.42 g (7.34 mmoles) of O-benzyl-N-methyl-amino-acetohydroxamic acid and then the pH is adjusted to 4.5 with 1N NaOH. 1.30 g (7.34 mmoles) of WSC are added as portions maintaining the pH at 4.5. After 22 hours of stirring at room temperature, the reaction solution is extracted three times with CHCl3. By evaporating the chloroform solution the O-benzylic amido derivative is obtained in form of white crystals, 1.15 g, (yield 47%). The thus obtained product is dissolved in 10 ml of methanol and catalitycally hydrogenated at 20° c. at room pressure in the presence of 10% Pd on carbon, whereby the expected compound is obtained in form of white crystals m.p. 107°–111° C., 0.7 g, yield 83%.

The compounds which are hereinafter listed have been prepared according to the previous examples but for sake of shortness their descriptions are not repeated, the chemical parameters of the same compounds being only reported.

In the further examples which follow, the examples 7, 8, 9, 10, 11, 12, and 13 have been carried out by repeating examples 4, starting from the suitable reactants.

The examples 14, 15 and 16, in turn, have been carried out by respectively repeating the example 1, 5 and 2.

EXAMPLE 7 trans-(1R,2R)-2[[N-[2-(hydroxyamino)-2-oxoethyl]N-ethylamino]carbonyl]-cyclohexanecarboxylic acid To a stirred solution of 2.0 g(11.6 mmol) of (1R,2R)(−)-1,2-cyclohexane-dicarxylic acid and 1.52 g (11.6 mmol) of ethyl N-ethylaminoacetate in 60 mL of THF at 5° C. were added 2.38 g (11.6 mmol) of DCC. The solution was stirred at 5° C. 2 h and at room temperature overnight. The percipitated dicyclohexylurea was filtered off, and the solvent was evaporated. The residual oil was dissolved in $CH_2Cl_2$, washed with water (10 mL) then with 15 mL of aqueous 5% $NaHCO_3$.

The aqueous extract was washed with $CH_2Cl_2$ (10 mL), was acidified with 6N HCl, then was extracted with 20 mL of $CH_2Cl_2$, and the extracts were dried($Na_2SO_4$) and evaporated to give the "amido-ester" intermediate: 1.9 g, 58% yield, oily crystals.

This intermediate was treated with hydroxylamine hydrochloride according to the procedure described in the Example 2, to give 1.38 g (87%) of pure title compound as a white solid: $[\alpha_D]^{10°} = 10.7$ (C 1.5 ethanol).

EXAMPLE 8

Cis-2[[N-[1-(2-phenylethyl)-2-(hydrxyamino)-2-oxoethyl]-N-methylamino]carbonyl]-cyclohexanecarboxylic acid To a stirred solution of 1.24 g (8.0 mmol) of cis-cyclohexanedicarboxylic anhydride in 50 mL of $CH_2Cl_2$ were slowly added at room temperature 100 mL of a $CH_2Cl_2$ solution containing 2.24 g (8.0 mmol) of O-benzyl-2-methylamino-4-phenyl-butanehydroxamic acid and 0.81 g(8.0 mmol) of triethylamine. The reaction mixture was then stirred for 5 h at room temperature. The $CH_2Cl_2$ was evaporated at reduced pressure and the residue was dissolved in aqueous 5% NaOH; acidification of this solution with concentrated HCl afforded 2.5 g (68%) of the "O-benzylic amide" intermediate, which was hydrogenated in 20 mL of methanol, with 0.24 g of 10%(Pd/C) at room pressure and temperature for 2 h.

After filtration of the catalyst, evaporation of the solvent in vacuo gave a residue which was dissolved in 10 mL of hot acetone, the acetonic solution was allowed to cool and the precipitated first crop (0.1 g) was filtered off.

The solution was allowed to stand 4 days at 0° C. when a second crop of crystals began to precipitate; the solid was collected by filtration (0.27 g) and was treated with hot acetone (20 mL) under stirring for half a hour. The hot suspension was filtered obtaining a white solid (m.p. 165°-169° C.) corresponding to one of two racemic compounds defined by title chemical name.

The acetonic filtrate was evaporated to give a residue which recrystallized from $CHCl_3$ gave a white solid (m.p.137°-139° C.) corresponding to the other racemic compound defined by the title chemical name.

EXAMPLE 9

Cis-(1S,2R)-2[[N-[2-(hydroxyamino)-2-oxoethyl]-N-methylamino]carbonyl]-cyclohexanecarboxylic acid 2-methoxycarbonyl-(1R,2S)-cyclohexanecarboxilic acid was obtained following the literature (P. Mohr et al., Helv.Chim.Acta, 1983,66,2501). $[\alpha]_{578}^{20} = +4.23°$ (C=5.5, ethanol);o.p.=63.1%.

A sample of half ester (2.7 g, 14.5 mmol) was dissolved in THF(10 mL) and cooled at 0° C. A solution of O-benzylsarcosinhydroxamic acidtrifluoroacetate (4.47 g, 14.5 mmol) and triethylamine (2 mL, 14.5 mmol) in $CHCl_3$ (10 mL), 1-hydroxy-benzotriazol (16-20% water, 2.45 g, 14.5 mmol) in THF (20 mL) and dicyclohexylcarbodiimide (3.29 g, 14.65 mmol) in THF (15 mL) were added successively. The solution was stirred at 0° C. for 1 h and at room temperature overnight. After filtration of dicyclohexylurea and evaporation of solvents of solvents, the residue was dissolved in AcOEt. After filtration of residual dicyclohexylurea, the solution was washed with water (2×20 mL), 10% citric acid (3×20 mL), water (20 mL), 5% $NaHCO_3$(3×20 mL) and water (20 mL). The organic layer was dried over $MgSO_4$ and evaporated in vacuo. The oil was purified by flash-chromatography (AcOEt/petroleum-ether=80/20). The oily product (2.55 g, 45%) showed $[\alpha]_{578}^{20} = +14.89°(C=6.2,$ ethanol). The oil (2.27 g, 6.27 mmol) was dissolved in 1M aqueous NaOH(50 mL) and the mixture was stirred two hours at room temperature. The solution was acidified with 10% HCl at 0° C. and extracted with $CHCl_3$ (3×30 mL). The organic layer was extracted with 5% $NaHCO_3$ (3×20 mL), the basic solution was acidified with 10% HCl AT 0° C. and extracted with $CHCl_3$ (3×20 ML). The organic layer was dried over $MgSO_4$ and evaporated in vacuo. The residue crystallized from aceton, giving a white solid (1.42 g, 65%); m.p. 110°-113° C.; $[\alpha]_{578}^{20} = +12.7°(C=5.0,$ Ethanol). The preceding compound (0.82 g, 2.36 mmol) was hydrogenated with 10% Pd on charcoal (100 mg) in methanol (40 mL) and, after filtration, the solvent was evaporated in vacuo. The residue crystallized from methanol/ether giving a white solid (300 mg, 50%): m.p. 127°-128° C., $[\alpha]_{578}^{20} = +26.1°$ (C=1.5, Ethanol).

EXAMPLE 10

Cis-2[[N-[1-benzyl-2-(methoxyamino)-2-oxoethyl]-N-methylamino]carbonyl] cyclohexanecarboxylic acid To a stirred suspension of 1.28 g(8.32 mmol) of cis-cyclohexanedicarboxylic anhydride in 50 ml of $CH_2Cl_2$ were added dropwise 120 mL of a $CH_2Cl_2$ solution containing 2 g(8.3 mmol) of N-methyl-O-methyl-phenylalanyl-hydroxamic acid (formate salt) and 0.84 g) (8.32 mmol) of triethyllamine, and the mixture was stirred at room temperature for 5H. The reaction mixture was washed twice with 5% HCl and with water, and then was extracted with 10% aqueous $NaHCO_3$. The extracts were cooled and acidified with concentrated HCl to give a solid which was recrystallized from methanol to yield the title compound as white crystals, m.p. 168°-171° C.

EXAMPLE 11

Trans-2[[N-[2-(N'-hydroxy-N'-methylamino)-2-oxoethyl]-N-ethylamino] carbonyl]-cyclohexanecarboxylic acid To a stirred solution of 4.28 g (15 mmol) of trans-2[[N-[2-(ethoxy)-2-oxoethyl]N-ethylamino]carbonyl]-cyclohexane-carboxilic acid (the "amido ester" intermediate described in the Example 2) in 21 mL of methanol at 5° C. were added 2.0 1 g (49.5 mmol) of NaOH dissolved in 21 mL of methanol and then 1.38 g (16.5 mmol) of N-methyl-hydroxylamine hydrochloride. After the mixture was stirred at 10° C. for 4 h, the solvent was removed in vacuo and the residue was dissolved in 10 ml of water and 10 mL of ethyl acetate. The stirred mixture was slowly acidified with 5% HCl, the organic layer was separated and the aqueous solution was extracted again with 10 ml of ethyl acetate. The extracts were dried (Na$_2$SO$_4$) and the solvent was distilled under reduced pressure to leave a residue which, recrystallized from ether, gave 3.4 g (79%) of the title compound as a white solid, m.p. 132° C.

EXAMPLE 12

Methyl-cis-2[[N-[2-(hydroxyamino)-2-oxoethyl]-N-methylamino]carbonyl]-cyclohexanecarboxylate 2-methoxycarbonyl-cyclohexanecarboxylica acid (1.5 g, 8.06 mmol) was dissolved in CH$_2$Cl$_2$ (10 mL) and a solution of O-bensyl-sarcosin-hydroxamic acid-trifluoroacetate (b 2.48 g, 8.06 mmol) and triethylamine (1.1 mL, 8.06 mmol) in CH$_2$Cl$_2$ (10 mL) was added. The solution was cooled at 0° C. and dicyclohexylcarbodiimide (1.66 g, 8.06 mmol) in CH$_2$Cl$_2$ (20 mL) was added with rapid stirring. After half hour at 0° C., the mixture was stirred at room temperature for 3 hours and the resulting dicyclohexylurea (DCU) was removed by filtration. After evaporation of the solvent, the residue was dissolved in AcOEt and, after filtration of residue DCU, was washed successively with water (30 mL), 10% citric acid (30×20 mL), water (30 mL), 5% NaHCO$_3$ (3×20 mL) and water (30 mL). The organic layer was dried over MgSO$_4$ and evaporated in vacuo. An oily product was obtained (1.85 g, 62%. The preceding compound (1.57 g, 4.34 mmol) was hydrogenated in methanol (50 mL) with 10% Pd on charcoal (0.15 g). After filtration of the catalyst, the solution was evaporated in vacuo and the oil was crystalized from aceton/-diethylether. A withe solid was obtained 0.71 g, 60%): m.p. 101°-102° C.

EXAMPLE 13

Trans -2[[N-[2-(acetyloxyamino)-2-oxoethyl-N-ethylamino]-carbonyl]-cyclohexanecarboxylic acid To a stirred suspension of 2.0 g (7.3 mmol) of trans -[[N-[2-(hydroxyamino)-2-oxoethyl]-N-ethylamino]carbonyl]-cyclohexanecarboxylic acid (Example 2) in 20 mL of CH$_2$Cl$_2$ at 5° C. were added 2.0 g (21.2 mmol) of acetic anhydride and then dropwise 1.48 g (14.7 mmol) of triethylamine. The obtained solution was then added with 0.04 g (0.36 mmol) of 4-N,N'-dimethylamino-pyridine and stirred at room temperature 3 h.

The reaction mixture was washed with 2×10 mL of aqueous 5% HCl, then with saturated aqueous NaCl (10 mL), dried (CaCl$_2$), and the solvent was evaporated. The residual oil was washed with ether and recrystallized from ether-CH$_2$Cl$_2$ (2:1) to give the title compound as white crystals m.p. 140°-141° C.

EXAMPLE 14

Cis-2-[[N-[2-(N'-acetoxy-N'-acetylamino)-2-oxoethyl]-N-methyl-amino]carbonyl]cyclohexanecarboxylic acid To a solution of the example 4 compound (330 mg, 1.28 mmol), triethylamine (0.55 ml, 3.95 mmol) and N,N-dimethylaminopyridine (10 mg amount) in dichloromethane (10 mL) stirred under nitrogen and cooled at 0° C., was added acetic anhydeide (270 mg, 2.65 mmol). The mixture was allowed to warm at room temperature and an aliquot was checked with ferric trichloride to verify the complete acylation of the hydroxamic moiety. Then the mixture was washed with 10% HCl (2×10 mL), 5% NaHCO$_3$ (2×10 mL), water dried with MgSO$_4$. The solvent was removed under reduced pressure at room temperature and the crude product was crystallized from diethylether to give a white solid (306 mg, 70%): m.p. 108°-109° C.

EXAMPLE 15 acetoxy methyl cis-2-[[N-[2-(hydroxyamino)-2-oxoethyl]-N-methyl-amino]carbonyl]cyclohexanecarboxylate A mixture of the example 4 "O-benzylic amide" intermediate (4.5 g, 13 mmol) and triethylamine (1.8 mL, 13 mmol) dissolved in anhydrous THF (30 mL) was aDDED dropwise under nitrogen, to a solution of iodomethylacetate (3.0 g, 15 mmol) in the some solvent (20 mL) cooled to −5° C. The mixture was stirred for 30 min and then allowed to warm at room temperature. The precipitated white solid was filtered off, and the filtrate was concentrated in vacuo. The residue was taken up in AcOEt (20 mL), washed with 5% NaCO$_3$ (2×20 mL), water and dried (MgSO$_4$).

The solvent was removed under reduced pressure to give the "O-benzylic acetoxy methyl" derivative (3.88 g, 71%) as a yellow viscous oil, which was hydrogenated (6 h) in THF (30 mL) in the presence of 10% Pd/C to give the title compound (quantitative amount) as a white glass.

EXAMPLE 16 methyl cis-2[[N-[2-(acetoxymethyloxy)amino-2-oxoethyl]-N-methylamino]carbonyl]cyclohexanecarboxylate To a stirred mixture of the example 12 compound (1 g, 3.6 mmol) and triethylamine (0.52 mL, 3.7 mmol) in anhydrous THF (25 mL) was added iodomethylacetate (0.74 g, 3.6 mmol) in the some solvent (10 mL) under nitrogen. The mixture was left at room temperature for 98 h. The precipitated solid was filtered off and most of the solvent was evaporated under reduced pressure. The residue was partitioned between dichloromethane and cold 5% aqueous HCl, the organic layer was washed with 5% HCl, 10% NaHCO$_3$, water and dried with MgSO$_4$.

The solvent was evaporated under reduced pressure to give the title compound (0.9 g, 79%) as a pale yellow oil.

In the further examples:
the compounds 17, 18, 19, 20, 21, 22, 23, 27, 28, 29, 30, 31, 32, 33 and 34 were prepared according to the Example 4 using the proper starting compounds;
the compound 24 according to the Example 1;
the compounds 25, 26, 36, 37, 38, 39, 40 and 41 according to the Example 2;
the compound 42 according to the Example 10;
the compounds 43, 44 and 45 according to the Example 11;
the compound 35 according to Example 8.

EXAMPLE 17

Cis-2-[[N-[3-(hydroxyamino)-3-oxopropyl]amino]carbonyl]-cyclohexane-carboxylic acid White crystals, m.p. 145°-148° C.

EXAMPLE 18

Cis-2[[N-[1-benzyl-2-(hydroxyamino)-2-oxoethyl-]amino]carbonyl]-cyclohexane carboxylic acid White crystals, m.p. 115°–118° C.

EXAMPLE 19

Cis-2[[N-[1-(2-phenylethyl)-2-(hydroxyamino)-2-oxoethyl]amino]carbonyl]cyclohexanecarboxylic acid White crystals, m.p. 83°–85° C.

EXAMPLE 20

Cis-2[[N-[1-(3-phenylpropyl)-2-(hydroxyamino)-2-oxoethyl]amino]carbonyl]-cyclohexanecarboxylic acid White crystals, m.p. 148°–150° C.

EXAMPLE 21

Trans-2-[[N-[2-(hydroxyamino)-2-oxoethyl]-N-methylamino]carbonyl]-cyclohexanecarboxylic acid.

White crystals, m.p. 172°–174° C.

EXAMPLE 22

Cis-2[[N-[1-(2-phenylethyl)-2-(hydroxyamino)-2-oxoethyl]amino]carbonyl] cyclopentanecarboxylic acid White crystals, m.p. 147°–148° C.

EXAMPLE 23

Cis-2[[N-[1-(3-phenylpropyl)-2-(hydroxyamino)-2-oxoethyl]amino]carbonyl]-cyclopentanecarboxylic acid White crystals, m.p. 122°–126° C.

EXAMPLE 24

Cis-2[[N-[2-benzyl-3-(hydroxyamino)-3-oxopropyl-]amino]carbonyl]cyclo-pentanecarboxylic acid Ivory crystals, m.p. 143°–146° C.

EXAMPLE 25

Trans-2[[N-[2-(hydroxyamino)-2-oxoethyl]-N-phenylamino]carbonyl]cyclo-hexanecarboxylic acid White crystals, m.p. 151°–152° C.

EXAMPLE 26

Cis-2[[N-[2-(hydroxyamino)-2-oxoethyl]-N-ethylamino]carbonyl]cyclohexane-carboxylic acid White crystals, m.p. 172°–174° C.

EXAMPLE 27

Cis-2[[N[1-methyl-2-(hydroxyamino)-2-oxoethyl]-N-methylamino]carbonyl]-cyclohexanecarboxylic acid Ivory crystals, m.p. 83°–84° C.

EXAMPLE 28

Trans-2[[N-[1-methyl-2-(hydroxyamino)-2-oxoethyl]-N-methylamino]carbonyl]-cyclohexanecarboxylic acid White crystals, m.p. 132°–134° C.

EXAMPLE 29

Cis-2[[N-[1-benzyl-2-(hydroxyamino)-2-oxoethyl]-N-methylamino]carbonyl]-cyclohexanecarboxylic acid Viscous oil.

EXAMPLE 30

Trans-2[[N-[1-benzyl-2-(hydroxyamino)-2-oxoethyl]-N-methylamino]carbonyl]-cyclohexanecarboxylic acid Ivory crystals, m.p. 144°–147° C.

EXAMPLE 31

Trans-2[[N-[1-(2-phenylethyl)-2-(hydroxyamino)-2-oxoethyl]-N-methylamino] carbonyl]-cyclohexanecarboxylic acid Viscous oil.

EXAMPLE 32

Cis-2[[N-[1-(3-phenylpropyl)-2-(hydroxyamino)-2-oxoethyl]-N-methylamino] carbonyl]-cyclohexanecarboxylic acid White crystals, m.p. 192° C. (dec.).

EXAMPLE 33

Trans-2[[N-[1-(3-phenylpropyl)-2-(hydroxyamino)-2-oxoethyl]-N-methylamino] carbonyl]-cyclohexanecarboxylic acid White crystals, m.p. 150°–155° C.

EXAMPLE 34

Cis-2[[N-[1-(2-phenylethyl)-2-(hydroxyamino)-2-oxoethyl]-N-methylamino] carbonyl]-cyclopentanecarboxylic acid White crystals, m.p. 150°–151° C.

EXAMPLE 35

Trans-2[[N-[1-benzyl-2-(hydroxyamino)-2 oxoethyl]-N-ethylamino]carbonyl]-cyclohexanecarboxylic acid.

Two racemic compounds:
colorless crystals, m.p. 167°–169° C.
Ivory crystals, m.p. 96° C. (dec.).

EXAMPLE 36

Trans-2[[N-[2-benzyl-3-(hydroxyamino)-3-oxopropyl]-N-ethylamino]carbonyl]-cyclohexanecarboxylic acid White solid, m.p. 94° C.

EXAMPLE 37

Cis-2[[N-[3-(hydroxyamino)-3oxopropyl]-N-ethylamino]carbonyl]-cyclohexane carboxylic acid Colorless crystals, m.p. 146°–148° C.

EXAMPLE 38

Trans-2[[N-[3-(hydroxyamino)-3-oxopropyl]-N-ethylamino]carbonyl]-cyclo hexanecarboxylic acid Colorless crystals, m.p. 148°–150° C.

EXAMPLE 39

Cis-2[[N-[2-(hydroxyamino)-2-oxoethyl]-N-propylamino]carbonyl]-cyclohexane carboxylic acid Colorless crystals, m.p. 84°–86° C.

EXAMPLE 40

Trans-2[[N-[2-(hydroxyamino)-2-oxoethyl]-N-propylamino]carbonyl]-cyclo hexanecarboxylic acid Colorless crystals, m.p. 132°–133° C.

EXAMPLE 41

Trans-2[[N-[2-(hydroxyamino)-2-oxoethyl]-N-(2-propyl)amino]carbonyl]-cyclo hexanecarboxylic acid Colorless crystals, m.p. 131° C.

EXAMPLE 42

Trans-2[[N-[1-benzyl-2-(methoxyamino)-2-oxoethyl]-N-methylamino]carbonyl]-cyclohexanecarboxylic acid White crystals, m.p. 100°-102° C.

EXAMPLE 43

Cis-2[[N-[2-(N'-hydroxy-N'-methylamino)-2-oxoethyl]-N-methylamino] carbonyl]-cyclohexanecarboxylic acid White crystals, m.p. 144° C.

EXAMPLE 44

Trans-2[[N-[2-(N'-hydroxy-N'-methylamino)-2-oxoethyl]-N-ethylamino] carbonyl]-cyclohexanecarboxylic acid Colorless crystals, m.p. 129° C.

EXAMPLE 45

Trans-2[[N-[3-(N'-methyl-N'-hydroxyamino)-3-oxopropyl]-N-ethylamino] carbonyl]-cyclohexanecarboxylic acid Viscous Oil The ACE-inhibiting activity of the compounds of the invention has been evaluated by determining the inhibition of the hydrolysis of the ippuril-glycil-glycine artificial substrate by the ACE contained in the rat serum. The IC50 values have been calculated by the regression analysis of the linear part of the log dose/percent inhibition curve.

In the following table the values of IC50 (nM) and ED50 i.v. of a group of compounds representative of the compounds of the invention have been reported.

Dose-dependent antihypertensive activity of selected compounds was calculated after intravenous administration to the anaesthetized ganglion-blocked rat. Inhibition of blood pressure increases induced by repeated i.v. injections of angiotensin I was measured and the ED50 values, reported in the table, were calculated at the time of maximum effect (1 min for all tested compounds).

Half-lives (t₁) of the antihypertensive action were also calculated and reported.

| No. Es. | ACE inhibition IC$_{50}$ (nM) | Antihypertensive activity ED50 i.v. mg kg | t½ min |
|---|---|---|---|
| 1 | 1600 | | |
| 4 | 6 | 0,035 | 15 |
| 9 | 3,5 | 0,016 | |
| 21 | 20 | 0,060 | 15 |
| 18 | 400 | | |
| 29 | 30 | | |
| 30 | 30 | | |
| 19 | 28000 | | |
| 8 | 62 | | |
| 3 | 3500 | | |
| 6 | 730 | | |
| 20 | 10000 | | |
| 32 | 135 | | |
| 26 | 25(15) | 0,113 | |
| 2 | 8 | 0,038 | 14 |
| 7 | 7,6 | 0,022 | |
| 14 | 280 | 1,5 | |
| coptopril | 1,2 | 0,011 | 9 |

The compound 4, as every ACE-inhibiting agent, has not influenced, on the contrary, the pressure answer to angiotensin II, up to the dose of 1 mg kg$_{i.v.}$.

If account is taken of the fact that the compounds of the present invention show a very low acute toxicity, with LD50 higher than 1000 mg/kg in the intravenous administration to the mice, it is evident that the compounds of the invention are suitable in an excellent manner for the therapeutical use, for which dosages of the same order of magnitude as captopril are foreseen.

The pharmaceutical compositions according to the invention, given the type of therapeutical use, are preferably in forms which can be administered by oral route (tablets, capsules and the like); they contain as active principle, a compound of the invention of formula (I) together with the conventional carriers and excipients.

The preparation of the pharmaceutical forms is carried out with the standard techniques of the art.

We claim:

1. A compound having the formula (I):

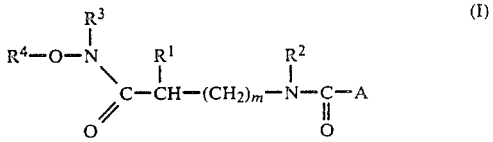

wherein

A represents

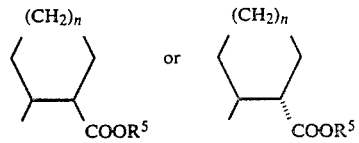

R¹ represents —H, —CH₃, —CH₂—CH₃, —CH(CH₃)₂,

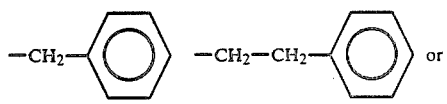

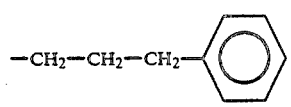

R₂ represents —H, CH₃, —CH₂—CH₃, —CH(CH₃)₂, —CH₂—CH₂—CH₃, —CH₂—CH(CH₃)₂ —CH₂—CH₂—CH₂—CH₃, —CH₂—CH₆H₅ or —C₆—H₅; R³ represents —H, —CH₃, —C₂H₅,

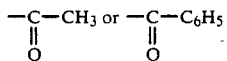

$R^5$ represents —H, —CH$_3$, —C$_2$H$_5$, —CH$_2$—C$_6$H$_5$ or

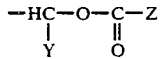

Y represents —H, —CH$_3$ or —CH(CH$_3$)$_2$
Z represents —H, —CH$_3$, —C(CH$_3$)$_3$, —CH(C$_2$H$_5$)$_2$,

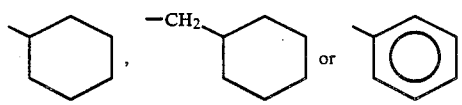

$R^4$ represents $R^5$ or

m is 0 or 1 and n is an integer varying between 0 and 3.

2. Compound of claim 1, wherein A represents a carboxy-substituted cyclohexane ring; $R^1$ is hydrogen; $R^2$ is methyl or ethyl; $R^3$ and $R^4$ are each hydrogen; $R^5$ is hydrogen or

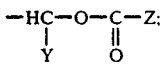

Y is hydrogen or methyl; Z is methyl tert-butyl or —CH(C$_2$H$_5$)$_2$; and m is zero.

3. Compound of claim 1, wherein said compound is cis-(1S,2R)-2[[N-[2-(hydroxyamino)-2-oxoethyl]-N-methylamino]carbonyl]-cyclohexanecarboxylic acid.

4. Compound of claim 1, wherein said compound is cis-2[[N-[2-(hydroxyamino)-2-oxoethyl]amino]carbonyl]cyclohexanecarboxylic acid.

5. Compound of claim 1, wherein said compound is trans-2[[N-[2-(hydroxyamino)-2-oxoethyl]-N-ethylamino]carbonyl]cyclohexanecarboxylic acid.

6. Compound of claim 1, wherein said compound is cis-2[[N-[2-(2-benzyl-3-(hydroxyamino)-3-oxopropyl]amino]carbonyl]cyclo-hexanecarboxylic acid.

7. Compound of claim 1, wherein said compound is cis-2[[N-[2-(hydroxyamino)-2-oxoethyl]-N-methylamino]carbonyl]cyclo-hexanecarboxylic acid.

8. Compound of claim 1, wherein said compound is cis-2[[N-[2-(hydroxamino)-2-oxoethyl]-N-phenylamino]carbonyl]cyclohexanecarboxylic acid.

9. Compound of claim 1, wherein said compound is trans-2[[N-[2-(hydroxyamino)-2-oxoethyl]-N-methylamino]carbonyl]cyclo-pentanecarboxylic acid.

10. Compound of claim 1, wherein said compound is trans-(1R,2R)-2[[N-[2-(hydroxyamino)-2-oxoethyl]-N-ethylamino]carbonyl]cyclohexanecarboxylic acid.

11. Compound of claim 1, wherein said compound is cis-2[[N-[1-(2-phenylethyl)-2-(hydroxyamino)-2-oxoethyl]-N-methylamino]carbonyl]cyclohexanecarboxylic acid.

12. Compound of claim 1, wherein said compound is cis-2[[N-[1-benzyl-2-(methoxyamino)-2-oxoethyl]-N-methylamino]carbonyl]cyclohexanecarboxylic acid.

13. Compound of claim 1, wherein said compound is trans-2[[N-[2-(N'-hydroxy-N'-methylamino)-2-oxoethyl]-N-ethylamino]carbonyl]cyclohexanecarboxylic acid.

14. Compound of claim 1, wherein said compound is methyl-cis-2[[N-[2-(hydroxyamino)-2-oxoethyl]-N-methylamino]carbonyl]cyclohexanecarboxylate.

15. Compound of claim 1, wherein said compound is trans-2[[N-[2-(acetyloxyamino)-2-oxoethyl]-N-ethylamino-]carbonyl]cyclohexanecarboxylic acid.

16. Compound of claim 1, wherein said compound is cis-2-[[N-2-(N'-acetoxy-N'-acetylamino)-2-oxoethyl]-N-methyl-amino]carbonyl]cyclohexanecarboxylic acid.

17. Compound of claim 1, wherein said compound is acetoxy methyl cis-2[[N-[2-(hydroxyamino)-2-oxoethyl]-N-methyl-amino]carbonyl]cyclohexanecarboxylate.

18. Compound of claim 1, wherein said compound is methyl cis-2[[N-[2-(acetoxymethyloxy)amino-2-oxoethyl]-N-methylamino]carbonyl]cyclohexanecarboxylate.

19. Compound of claim 1, wherein said compound is cis-2[[N-[3-(hydroxyamino)-3-oxopropyl]amino]carbonyl]cyclohexanecarboxylic acid.

20. Compound of claim 1, wherein said compound is cis-2[[N-[1-benzyl-2-(hydroxyamino)-2-oxoethyl-]amino]carbonyl]cyclohexanecarboxylic acid.

21. Compound of claim 1, wherein said compound is cis-2[[N-[1-(2-phenylethyl)-2-(hydroxyamino)-2-oxoethyl]amino]carbonyl]cyclohexanecarboxylic acid.

22. Compound of claim 1, wherein said compound is cis-2[[N-[1-(3-phenylpropyl)-2-(hydroxyamino)-2-oxoethyl]amino]carbonyl]cyclohexanecarboxylic acid.

23. Compound of claim 1, wherein said compound is trans-2[[N-[2-(hydroxyamino)-2-oxoethyl]-N-methylamino]carbonyl]cyclohexanecarboxylic acid.

24. Compound of claim 1, wherein said compound is cis-2[[N-(1-(2-phenylethyl)-2-(hydroxyamino)-2-oxoethyl]amino]carbonyl]cyclopentanecarboxylic acid.

25. Compound of claim 1, wherein said compound is cis-2[[N-[1-(3-phenylpropyl)-2-(hydroxyamino)-2-oxoethyl]amino]carbonyl]cyclopentanecarboxylic acid.

26. Compound of claim 1, wherein said compound is cis-2[[N-[2-benzyl-3-(hydroxyamino)-3-oxopropyl]amino]carbonyl]cyclopentanecarboxylic acid.

27. Compound of claim 1, wherein said compound is trans-2[[N-[2-(hydroxyamino)-2-oxoethyl]-N-phenylamino]carbonyl]cyclohexanecarboxylic acid.

28. Compound of claim 1, wherein said compound is cis-2[[N-[2-(hydroxyamino)-2-oxoethyl]-N-ethylamino]carbonyl]cyclohexanecarboxylic acid.

29. A compound of claim 1, wherein said compound is cis-2[[N-[1-methyl-2-(hydroxyamino)-2-oxoethyl]-N-methylamino]carbonyl]cyclohexanecarboxylic acid.

30. Compound of claim 1, wherein said compound is trans-2[[N-[1-methyl-2-(hydroxyamino)-2-oxoethyl]-N-methylamino]carbonylcyclohexanecarboxylic acid.

31. Compound of claim 1, wherein said compound is cis-2[[N-[1-benzyl-2-(hydroxyamino)-2-oxoethyl]-N-methylamino]carbonyl]cyclohexanecarboxylic acid.

32. Compound of claim 1, wherein said compound is trans-2[[N-[1-benzyl-2-(hydroxyamino)-2-oxoethyl]-N-methylamino]carbonyl]cyclohexanecarboxylic acid.

33. Compound of claim 1, wherein said compound is trans-2[[N-[1-(2-phenylethyl)-2-(hydroxyamino)-2-oxoethyl]-N-methyllamino]carbonyl]-cyclohexanecarboxylic acid.

34. Compound of claim 1, wherein said compound is cis-2[[N-[1-(3-phenylpropyl)-2-(hydroxyamino)-2-oxoethyl]-N-methylamino]carbonyl-cyclohexanecarboxylic acid.

35. Compound of claim 1, wherein said compound is trans-2[[N-[1-(3-phenylpropyl)-2-(hydroxyamino)-2-oxoethyl]-N-methylamino]carbonyl]-cyclohexanecarboxylic acid.

36. Compound of claim 1, wherein said compound is cis-2[[N-[1-(2-phenylethyl)-2-(hydroxyamino)-2-oxoethyl]-N-methylamino]carbonyl]-cyclopentanecarboxylic acid.

37. Compound of claim 1, wherein said compound is trans-2[[N-[1-benzyl-2-(hydroxyamino)-2-oxoethyl]-N-ethylamino]carboxyl]cyclohexanecarboxylic acid.

38. Compound of claim 1, wherein said compound is trans-2[[N-[2-benzyl-3-(hydroxyamino)-3-oxopropyl]-N-ethylamino]carbonyl]cyclohexanecarboxylic acid.

39. Compound of claim 1, wherein said compound is cis-2[[N-[3-(hydroxyamino)-3-oxopropyl]-N-ethylamino]carbonyl]cyclohexanecarboxylic acid.

40. Compound of claim 1, wherein said compound is trans-2[[N-[3-(hydroxyamino)-3-oxopropyl]-N-ethylamino]carbonyl]cyclohexanecarboxylic acid.

41. Compound of claim 1, wherein said compound is cis-2[[N-[2-(hydroxyamino)-2-oxoethyl]-N-propylamino]carbonyl]cyclohexanecarboxylic acid.

42. Compound of claim 1, wherein said compound is trans-2[[N-[2-(hydroxyamino)-2-oxoethyl]-N-propylamino]carbonyl]cyclohexanecarboxylic acid.

43. Compound of claim 1, wherein said compound is trans-2[[N-[2-(hydroxyamino)-2l-oxoethyl]-N-(2-propyl)amino]carbonyl]cyclohexanecarboxylic acid.

44. Compound of claim 1, wherein said compound is trans-2[[N-[1-benzyl-2-(methoxyamino)-2-oxoethyl]-N-methylamino]carbonyl]cyclohexanecarboxylic acid.

45. Compound of claim 1, wherein said compound is cis-2[[N-[2-(N'-hydroxy-N'-methylamino)-2-oxoethyl]-N-methylamino]carbonyl]cyclohexanecarboxylic acid.

46. Compound of claim 1, wherein said compound is trans-2[[N-(2-(N'-hydroxy-N'-methylamino)-2-oxoethyl]-N-ethylamino]carbonyl]cyclohexanecarboxylic acid.

47. Compound of claim 1, wherein said compound is trans-2[[N-[3-(N'-methyl-N'-hydroxyamino)-3-oxopropyl]-N-ethylamino]carbonyl]cyclohexanecarboxylic acid.

48. Compound of claim 2, wherein $R^5$ is hydrogen.
49. Compound of claim 48, wherein $R^2$ is ethyl.
50. Compound of claim 48, wherein $R^2$ is methyl.

* * * * *